United States Patent [19]
Liao

[11] Patent Number: 5,985,617
[45] Date of Patent: *Nov. 16, 1999

[54] MICROORGANISMS AND METHODS FOR OVERPRODUCTION OF DAHP BY CLONED PPS GENE

[76] Inventor: James C. Liao, 10573 Wellworth Ave., Los Angeles, Calif. 90024

[*] Notice: This patent is subject to a terminal disclaimer.

[21] Appl. No.: 09/277,183

[22] Filed: Mar. 26, 1999

Related U.S. Application Data

[63] Continuation of application No. 08/801,454, Feb. 18, 1997, Pat. No. 5,906,925.

[51] Int. Cl.$^6$ .............................. C12P 19/00; C12P 13/22; C12N 9/24; C12N 15/31
[52] U.S. Cl. ........................... 435/72; 435/108; 435/200; 536/23.7; 536/24.1
[58] Field of Search ............................ 435/72, 108, 200; 536/23.7, 24.1

[56] References Cited

U.S. PATENT DOCUMENTS 5,168,055  12/1992  Frost ........................................ 435/472
5,272,073  12/1993  Frost et al. .............................. 435/155

OTHER PUBLICATIONS

R. Patnaik, et al., "Pathway Engineering for Production of Aromatics in *Escherichia coli*: Confirmation of Stoichiometric Analysis by Independent Moduation of AroG, thtA, and Ppl Activities." Biotechnology and Bioengineering 361–370 (1995).
J.W. Frost, et al., Prospects for Biocatalytic Synthesis of Aromatics in the 21st Century, 18 New J. Chem. 341–348 (1994).
R. Patnaik, et al., "Engineering of *Escherichia coli* Central Metabolism for Aromatic Metabolite Production with Near Theoretical Yield," 60 App, Env. Microbiol. 3903–3908 (1994).
Y–P Chao, et al., "Alernation of Growth Yield by Overexerpression of Phosphoenolypruvate Carboxylase and Phosphoenolpyrute Carboxykinase in *Escherichia coli*", 59 App. Env. Microbiol. 4261–4265 (1993).
Y–P Chao, et al., "Characterization of *Escherichia coli* with Redirected Phosphoenolypyruvate Metabolism," Abstr. Pap. Am. Chem. Sol. 1992, 203 (1–3), abstract 49.
Y–P Chao, et al., "Control of Gluconeogenic Growth by pps and pck in *Escherichia coli*," 175 J. Bacteriol. 6939–6944 (1993).

K.M. Draths, et al., "Biocatalysis and Nineteenth Century Organic Chemistry: Conversion of D–glucose into Quinoid Organics," 114 J. Am. Chem. Soc. 9725–9726 (1992).
K.M. Draths, et al., "Biocatalytic Synthesis of Aromatics from D–glucose: The Role of Transketolase," 115 J. AM. Chem. Soc. 1956–1962 (1992).
R. Patnaik, et al., "The Phosphoenolpyruvate/Pyruvate Futile Cycle in *Escherichia coli*," Abstr. Pap. Am. Chem. Soc. 1992, 203(1–3), abstract 48.
K.M. Draths, et al., "Conversion of D–Glucose into Catechol: The Not–So–Common Pathway of Aromatic Biosynthesis," 113 J. Am. Chem. Soc. 9361–9363 (1991).
B.A. Castilho, et al., "Plasmid Insertion Mutagenesis and lac Gene Fusion with Mini–Mu Bacteriophage Transposons," 158 J. Bacteriol. 488–495 (1984).
R. Schoner, et al., 3–Deoxy–D–arabino–heptulosante 7–Phospate Synthase; Puritication, Properties, and Kinetics of the Tyrosine–Sensitive Isoenzyme from *Escherichia coli*, 251 J. Biol. Chem. 5440–5447 (1976).
E. Gollubm et al., "Assay for 3–Deoxy–arabino–heptulosonic acid 7–phosphate syntahse," 17A Methods Enzymol. 349–350 (1971).
Lehniger Biochemistry Second Edition p. 405 Worth Publishers Inc. (1975).
Patnaik et al., J. of Bacteriology 174 7527–7532 (1992) Stimulation of Glucose Catabolism in *Escherichia coli* by . . .
Amann et al, Gene 69 301–315 (1988) Tightly regulated tac promoter vectors . . .
Tobey et al., J. Biol. Chem. 261 12179–12183 (1986) The Nucleotide Sequence of the serA gene . . .
Neidhardt et al. *Escherichia coli* and Salmonella Typhimurium American Society for Microbiology (1987) pp. 369–413.
Nelms et al., Applied and Environmental Microbiology 58 2592–2598 (1992) Novel Mutations in the pheA Gene . . .
Draths et al., J. Am. Chem. Soc. 114 9725–9726 (1992) Biocatalysis and Nineteenth Century Organic Chemistry . . .
Harmon et al., Journal of Virology 66 5242–5247 (1992) Polyprotein Processing in cis and in trans by Hepatitis A virus . . .

*Primary Examiner*—John S. Brusca
*Attorney, Agent, or Firm*—Gunn & Associates

[57] ABSTRACT

Genetic elements comprising expression vectors and a gene coding for phosphoenol pyruvate synthase is utilized to enhance diversion of carbon resources into the common aromatic pathway and pathways branching therefrom. The overexpression of phosphoenol pyruvate synthase increases DAHP production to near theoretical yields.

29 Claims, 6 Drawing Sheets

MICROORGANISMS AND METHODS FOR OVERPRODUCTION OF DAHP BY CLONED PPS GENE

This is a Continuation of U.S. patent application Ser. No. 08/801,454 filed on Feb. 18, 1997 U.S. Pat. No. 5,906,925.

GOVERNMENT RIGHTS

This work was supported in part by the National Science Foundation (Grant BCS-9257351), the Welch Foundation (Grant A-1251), and the Texas Higher Education Coordinating Board (Grant 999903-084). The United States Government may own non-exclusive rights in and to the invention.

FIELD OF THE INVENTION

The present invention relates to the biosynthetic production of organic chemical compounds. In particular, the present invention relates to methods for increasing the yield of 3-deoxy-D-arabino-heptulosonate 7-phosphate (DAHP) in microorganisms through genetic alterations. The present invention also relates to methods of enhancing the production of cyclic and aromatic metabolites derived from DAHP in microorganisms through genetic alterations. For example, the biosynthesis of DAHP is the first step in the common aromatic pathway from which tyrosine, tryptophan, phenylalanine, and other aromatic metabolites are formed. Also, pathways branching from the common aromatic pathway provide such useful chemical products as catechol and quinoid organics such as quinic acid, benzoquinone, and hydroquinone. In addition, aspartame and indigo can be produced from products derived from the common aromatic pathway.

BACKGROUND OF THE INVENTION

Production of chemicals from microorganisms has long been an important application of biotechnology. Typically, the steps involved in developing a microorganism production strain include (i) selection of a proper host microorganism, (ii) elimination of metabolic pathways leading to by-products, (iii) deregulation of such pathways at both the enzyme activity level and the transcriptional level, and (iv) overexpression of appropriate enzymes in the desired pathways.

The last three steps can now be achieved by use of a variety of in vivo and in vitro methods. These methods are particularly user-friendly in well-studied microorganisms such as *Escherichia coli* (*E. coli*). Therefore, many examples of engineered microorganisms for physiological characterization and metabolite production have been published.

In most cases, the first target for engineering is the terminal pathway leading to the desired product, and the results are usually successful. However, further improvements of productivity (product formation rate) and yield (percent conversion) of desired products call for the alteration of central metabolic pathways which supply necessary precursors and energy for the desired biosyntheses of those products.

Cyclic and aromatic metabolites such as tryptophan, phenylalanine, tyrosine, quinones, and the like trace their biosynthesis to the condensation reaction of phosphoenolpyruvate (PEP) and D-erythrose 4-phosphate (E4P) to form DAHP. DAHP biosynthesis is the first committed step in the common aromatic pathway. DAHP biosynthesis is mediated by three DAHP synthases or isoenzymes. These isoenzymes are coded by genes aroF, aroG, and aroH, whose gene products are feed-back inhibited by tyrosine, phenylalanine and tryptophan, respectively.

After DAHP biosynthesis, some DAHP is converted to chorismate. Chorismate is an intermediate in biosynthetic pathways that ultimately leads to the production of aromatic compounds such as phenylalanine, tryptophan, tyrosine, folate, melanin, ubiquinone, menaquinone, prephenic acid (used in the production of the antibiotic bacilysin) and enterochelin. Because of the large number of biosynthetic pathways that depend from chorismate, the biosynthetic pathway utilized by organisms to produce chorismate is often known as the "common aromatic pathway".

Besides its use in chorismate production, DAHP can also be converted to quinic acid, hydroquinone, benzohydroquinone, or catechol as described by Draths et al. (Draths, K. M., Ward, T. L., Frost, J. W., "Biocatalysis and Nineteenth Century Organic Chemistry: conversion of D-Glucose into Quinoid Organics," *J. Am. Chem. Soc.*, 1992, 114, 1925–26). These biosynthetic pathways branch off from the common aromatic pathway before shikimate is formed.

The efficient production of DAHP by a microorganism is important for the production of aromatic metabolites because DAHP is the precursor in major pathways that produce the aromatic metabolites. The three aromatic amino acids, besides being essential building blocks for proteins, are useful precursor chemicals for other compounds such as aspartame, which requires phenylalanine. Additionally, the tryptophan pathway can be genetically modified to produce indigo.

The production of tryptophan and phenylalanine by *E. coli* has been well documented. For example, Aiba et al. (Aiba, S., H. Tsunekawa, and T. Imanaka, "New Approach to Tryptophan Production by *Escherichia coli*: Genetic Manipulation of Composite Plasmids In Vitro," *Appl. Env. Microbiol.* 1982, 43:289–297) have reported a tryptophan overproducer that contains overexpressed genes in the tryptophan operon in a host strain that is trpR and tna (encoding tryptophanase) negative. Moreover, various enzymes, such as the trpE gene product, have been mutated to resist feedback inhibition. Similar work has been reported for phenylalanine production.

In the past, the enhanced commitment of cellular carbon sources entering and flowing through the common aromatic pathway has been accomplished with only modest success (i.e., such attempts have fallen far below the theoretical yield). Typically, the enhancements were accomplished, by transferring into host cells, genetic elements encoding enzymes that direct carbon flow into and/or through the common aromatic pathway. Such genetic elements can be in the form of extrachromosomal plasmids, cosmids, phages, or other replicons capable of transforming genetic elements into the host cell.

U.S. Pat. No. 5,168,056 to Frost described the use of a genetic element containing an expression vector and a gene coding for transketolase (Tkt), the tkt gene. This genetic element can be integrated into the microorganisms chromosome to provide overexpression of the Tkt enzyme.

Additional examples include: Miller et al. (Miller, J. E., K. C. Backman, J. M. O'Connor, and T. R. Hatch, "Production of phenylalanine and organic acids by PEP carboxylase-deficient mutants of *Escherichia coli*," *J. Ind. Microbiol.*, 1987, 2:143–149) who attempted to direct more carbon flux into the amino acid pathway by use of a phosphoenolpyruvate carboxylase (coded by ppc) deficient mutant; Draths et al. (Draths, K. M., D. L. Pompliano, D. L. Conley, J. W. Frost, A. Berry, G. L. Disbrow, R. J. Staversky, and J. C. Lievense, "Biocatalytic synthesis of aromatics from D-glucose: The role of transketolase," *J. Am. Chem. Soc.*, 1992,114:3956–3962) who reported that overexpression of transketolase (coded by tktA) and a feed-back resistant DAHP synthase (coded by aroG$^{fbr}$) resulted in improved production of DAHP from glucose.

The overproduction of transketolase in tkt transformed cells has been found to provide an increased flow of carbon resources into the common aromatic pathway relative to carbon resource utilization in whole cells that do not harbor such genetic elements. However, the increased carbon flux may be further enhanced by additional manipulation of the host strain.

Thus, it is desirable to develop genetically engineered strains of microorganisms that are capable of enhancing the production of DAHP to near theoretical yield. Such genetically engineered strains can then be used for selective production of DAHP or in combination with other incorporated genetic material for selective production of desired metabolites. Efficient and cost-effective biosynthetic production of chorismate, quinic acid, hydroquinone, benzohydroquinone, catechol, or derivatives of these chemicals requires that carbon sources such as glucose, lactose, galactose, xylose, ribose, or other sugars be converted to the desired product in high yields. Accordingly, it is valuable from the standpoint of industrial biosynthetic production of metabolites to increase the influx of carbon sources for cell biosynthesis of DAHP and its derivatives.

SUMMARY OF THE INVENTION

The present invention provides genetically engineered strains of microorganisms that overexpress the pps gene for increasing the production of DAHP to near theoretical yields. The present invention also provides genetically engineered strains of microorganisms where at least one of the plasmids pPS341, pPSL706, pPS706, or derivatives thereof is transformed into a microorganism for increasing the production of DAHP to near theoretical yields.

The present invention further provides a method for increasing carbon flow for the biosynthesis of DAHP in a host cell comprising the steps of transforming into the host cell recombinant DNA comprising a pps gene so that Pps is expressed at enhanced levels relative to wild type host cells, concentrating the transformed cells through centrifugation, resuspending the cells in a minimal, nutrient lean medium, fermenting the resuspended cells, and isolating DAHP from the medium.

The present invention further provides methods of increasing carbon flow into the common aromatic pathway of a host cell comprising the step of transforming the host cell with recombinant DNA comprising a pps gene so that Pps is expressed at appropriate point in the metabolic pathways at enhanced levels relative to wild type host cells.

The present invention further provides methods for enhancing a host cell's biosynthetic production of compounds derived from the common aromatic pathway relative to wild type host cell's biosynthetic production of such compound, said method comprising the step of increasing expression in a host cell of a protein catalyzing the conversion of pyruvate to PEP.

The present invention also provides methods for overexpressing Pps in microorganism strains which utilize DAHP in the production DAHP of metabolites.

The present invention further provides a culture containing a microorganism characterized by overexpressing Pps where the culture is capable of producing DAHP metabolites near theoretical yields upon fermentation in an aqueous resuspension, minimal, nutrient lean medium containing assimilable sources of carbon, nitrogen and inorganic substances.

The present invention further provides a genetic element comprising a pps gene and one or more genes selected from the group consisting of an aroF gene, aroG gene, aroH gene, and an aroB gene.

The present invention further provides a DNA molecule comprising a vector carrying a gene coding for Pps.

DETAILED DESCRIPTION OF THE INVENTION

Many microorganisms synthesize aromatic precursors and aromatic compounds from the condensation reaction of PEP and E4P to produce DAHP. This condensation reaction to form DAHP is the first committed step in the biosynthetic pathway known as the common aromatic pathway. From this pathway, cells synthesize many cyclic metabolites, pre-aromatic metabolites, and aromatic metabolites, such as the aromatic amino acids, quinone biomolecules, and related aromatic and cyclic molecules.

The inventor have found that cell lines can be developed that increase the carbon flux into DAHP production and achieve near theoretical yields of DAHP by overexpressing phosphoenolpyruvate synthase (Pps) in the cell lines. Overexpression of Pps can increase the final concentration and yield of DAHP by as much as two-fold, to a near theoretical maximum as compared to wild type cell lines. The overexpression of Pps is achieved by transforming a cell line with recombinant DNA comprising a pps gene so that Pps is expressed at enhanced level relative to the wild type cell line and so that the yield of DAHP approaches its theoretical value.

Generally, the present invention enhances expression in a host cell of Pps relative to a wild type host cell either by the transfer and stable incorporation of an extrachromosomal genetic element into the host cell or by the transfer of the genetic element into the genome of the host cell. The expressed gene products are enzymes configured to provide appropriate catalytic sites for substrate conversion of common aromatic pathway compounds.

Besides the use of the pps gene, the present invention also provides for transfer of genetic elements comprising the tkt gene, the gene coding for DAHP synthase (aroF in *E. coli*), the gene coding for 3-dehydroquinate synthase (aroB in *E. coli*), or other genes encoding enzymes that catalyze reactions in the common aromatic pathway. Such a cell transformation can be achieved by transferring one or more plasmids that contain genes that code for enzymes that increase the carbon flux for DAHP synthesis and for subsequent synthesis of other desired cyclic, pre-aromatic, and aromatic metabolites. As a result of this transfer of genetic element(s), more carbon enters and moves through the common aromatic pathway relative to wild type host cells not containing the genetic elements of the present invention.

In one embodiment, the present invention comprises a method for increasing carbon flow into the common aromatic pathway of a host cell by increasing the production of DAHP through the overexpression of Pps at the appropriate point in the common aromatic pathway to provide additional PEP at the point where PEP condenses with E4P. Increasing carbon flow requires the step of transforming the host cell with recombinant DNA containing a pps genes so that Pps is overexpressed at enhanced levels relative to wild type host cells. DAHP is then produced by fermentation of the transformed cell in a nutrient medium which the DAHP can be extracted from the medium on a batch wise or continuous extraction procedure.

In another embodiment, the present invention involves the co-overexpression of a pps gene and other genes coding for enzymes of the common aromatic pathway where additional genetic material is transformed into the host cell. The genes transferred can include the tkt gene, DAHP synthase gene and DHQ synthase gene (preferably the aroF or aroB genes, respectively). Although the work so far has centered around transforming certain host cell strains of *E. coli* such as AB2847 aroB, this particular host cell may not be the preferred host cell for the commercial production of DAHP or DAHP metabolites through the overexpression of Pps.

Another embodiment of the present invention is a method for enhancing a host cell's biosynthetic production of compounds derived from the common aromatic pathway. This method involves the step of increasing expression of Pps in the host cell relative to a wild type host cell. The step of increasing expression of Pps can include transferring into the host cell a vector carrying the pps gene. The overexpression of Pps results in forcing increased carbon flow into the biosynthesis of DAHP.

In another embodiment of the present invention, a method for enhancing a host cell's biosynthetic production of compounds derived from the common aromatic pathway relative to wild type host cell's biosynthetic production of such compound is provided. This method requires the step of increasing expression in a host cell of a protein catalyzing conversion of pyruvate to PEP. The expression of such a protein can involve transferring into the host cell recombinant DNA including a pps gene.

In another preferred embodiment, the present invention comprises a genetic element comprising the pps gene and a gene selected from the group consisting of a aroF gene, a aroB gene, and a tkt gene. Such a genetic element can comprise plasmid pPS341, a vector carrying a pps gene.

To channel more carbon flux into the common aromatic pathway, the inventor has found that PEP production in a given cell line must be increased. This increase can be achieved by deactivating pathways competing for PEP or by recycling pyruvate back into PEP.

Besides being used in the biosynthesis of DAHP, PEP is used as a phosphate donor in the phosphotransferase system (PTS) which is responsible for glucose uptake. Additionally, PEP can be converted to pyruvate by pyruvate kinases and to oxaloacetate by phosphoenolpyruvate carboxylase. All such competing pathways limit the availability of PEP for the biosynthesis of DAHP and all metabolites derived from the common aromatic pathway or pathways branching therefrom.

Once PEP is converted to pyruvate by either PTS or pyruvate kinases, pyruvate is not generally recycled back to PEP because of a high energy cost. As a result, a large amount of carbon flux is channeled from PEP through pyruvate and eventually to organic acids, carbon dioxide, or cell mass.

PEP is critical for the biosynthesis of DAHP and DAHP metabolites including all metabolites from the common aromatic pathway. The first committed step of the common aromatic pathway involves the formation of DAHP from the condensation of E4P and PEP. This condensation involves an aldol condensation between an intermediate carbanion of C-3 of PEP and the carbonyl C-1 of E4P. The majority of the PEP molecules react stereospecifically with respect to the configuration on C-3.

A key component of the methods of the present invention directed at increased carbon flux commitment to DAHP and DAHP metabolites is the recycling of pyruvate to PEP. Pyruvate is available in host cells as an end product of glycolysis.

In glycolysis, the free energy of degradation of glucose to pyruvate is utilized to synthesize ATP. Broadly speaking, this process involves an investment of ATP to form a phosphoryl compound (FBP) from glucose, which is then cleaved to two $C_3$ units. The free energy of this reaction is used in the oxidation of GAP which is then utilized to synthesize an acyl phosphate, a "high-energy" intermediate (1,3-BPG). 1,3-BPG is used to phosphorylate ADP to ATP. The second "high-energy" compound of the pathway, PEP, which is produced from 2PG, also phosphorylates ADP to ATP. Thus, the degradation of glucose via the glycolytic pathway produces pyruvate. The overall reaction of glycolysis is therefore:

The first step of glycolysis is the transfer of a phosphoryl group from ATP to glucose to form glucose-6-phosphate (G6P) in a reaction catalyzed by hexokinase. Hexokinase is a relatively nonspecific enzyme contained in all cells that catalyzes the phosphorylation of hexoses such as D-glucose, D-mannose, and D-fructose. The second substrate for hexokinase, as with other kinases, is an $Mg^{2+}$-ATP complex. In fact, uncomplexed ATP is a potent competitive inhibitor of hexokinase.

Hexokinase has a Random Bi Bi mechanism in which the enzyme forms a ternary complex with glucose and $Mg^{2+}$-ATP before the reaction occurs. By complexing with the phosphate oxygen atoms, the $Mg^{2+}$ is thought to shield their negative charges, making the phosphorus atom more accessible for the nucleophilic attack of the C(6)—OH group of glucose.

Next G6P is converted to fructose 6-phosphate (F6P) by phosphoglucose isomerase (PGI). This reaction is an isomerization of an aldose to a ketose. Since G6P and F6P both exist predominantly in their cyclic forms, the reaction requires ring opening, followed by isomerization, and subsequent ring closure. The overall reaction is thought to occur by enzyme mediated general acid-base catalysis.

Next, phosphofructokinase (PFK) phosphorylates F6P to yield fructose 1,6-bisphosphate (FBP or F1,6P). PFK catalyzes the nucleophilic attack by the C(1)—OH group of F6P on the electrophilic γ-phosphorus atom of the $Mg^{2+}$-ATP complex.

PFK plays a central role in control of glycolysis because it catalyzes one of the pathway's rate-determining reactions. In many organisms the activity of PFK is enhanced allosterically by several substances, including AMP, and inhibited allosterically by several other substances, including ATP and citrate. The regulatory properties of PFK are exquisitely complex.

Aldolase then catalyzes the cleavage of FBP to form the two trioses glyceraldehyde-3-phosphate (GAP) and dihydroxyacetone phosphate (DHAP). This reaction is an aldol cleavage (the reverse of an aldol condensation). The aldol cleavage between C(3) and C(4) of FBP requires a carbonyl at C(2) and hydroxyl at C(4).

Only one of the products of the aldol cleavage reaction, GAP, continues along the glycolytic pathway. However, DHAP and GAP are ketose-aldose isomers just as are F6P and G6P. Interconversion of GAP and DHAP is therefore possible via an enediolate intermediate analogous to the phosphoglucomutase reaction. Triose phosphate isomerase (TIM) catalyzes this process.

At this point, the glucose which has been transformed into two GAPs, has completed the preparatory stage of glycolysis. This process has required the expenditure of two ATPs. However, this investment has resulted in the conversion of one glucose into two $C_3$ units, each of which has a phosphoryl group that, with a little chemical artistry, can be converted to a "high-energy" compound whose free energy of hydrolysis can be coupled to ATP synthesis. This energy investment will be doubly repaid in the final stage of glycolysis in which the two phosphorylated $C_3$ units are transformed to two pyruvates with the coupled synthesis of four ATPs per glucose.

The next step in glycolysis involves the oxidation and phosphorylation of GAP by $NAD^+$ and P, as catalyzed by glyceraldehyde 3-phosphate dehydrogenase (GAPDH). In this reaction, aldehyde oxidation, an exergonic reaction, drives the synthesis of the acryl phosphate 1,3-diphosphyglycerate (1,3-DPG).

The next reaction of the glycolytic pathway results in the first formation of ATP together with 3-phosphoglycerate (3PG) in a reaction catalyzed by phosphoglycerate kinase (PGK):

3PG is then converted to 2-phosphoglycerate (2PG) by phosphoglycerate mutase (PGM). This reaction is necessary preparation for the next reaction in glycolysis, which generates a "high-energy" phosphoryl compound for use in ATP synthesis.

Subsequently, 2PG is dehydrated to phosphoenolpyruvate (PEP) in a reaction catalyzed by enolase. The enzyme forms a complex with a divalent cation such as $Mg^{2+}$ before the substrate is bound. Fluoride ion inhibits glycolysis with the accumulation of 2PG and 3PG. It does so by strongly inhibiting enolase in the presence of $P_i$. The inhibitory species is fluorophosphate ion ($FPO_3^{3-}$), which probably complexes the enzyme-bound $Mg^{2+}$ thereby inactivating the enzyme. Enolase's substrate 2PG, therefore builds up and as it does so, is equilibrated with 3PG by PGM.

Finally, pyruvate kinase (PK) couples the free energy of PEP hydrolysis to the synthesis of ATP to form pyruvate. At this point, glycolysis has produced PEP, one of the precursors to DAHP production and the entry way to the common aromatic pathway.

Besides PEP, DAHP biosynthesis, as well as that of other products derived from the common aromatic pathway and pathways branching therefrom, depends on the biosynthesis of E4P.

Figure 4:
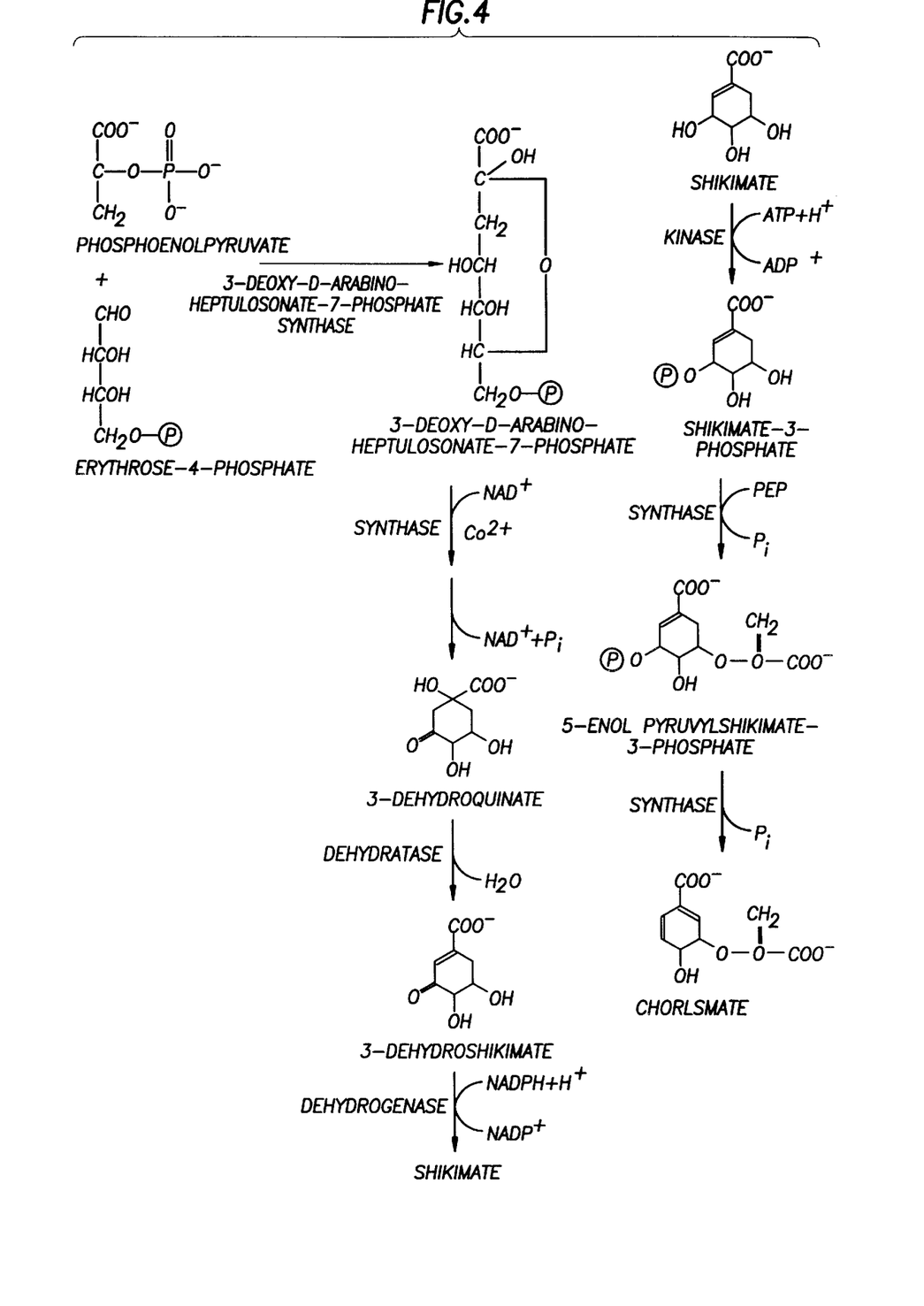
FIG. 4. The common aromatic pathway is shown whereby E4P and PEP under go a condensation reaction to initiate the common aromatic pathway.

With reference to FIG. 4, E4P is a biosynthetic intermediate of the pentose phosphate pathway. The pentose phosphate pathway is situated between glycolysis and a variety of different biosynthetic cascades. This pathway yields E4P via a nonoxidative branch of the pathway. The nonoxidative pentose phosphate pathway converts D-fructose 6-phosphate into varying equivalents of D-ribose 5-phosphate, D-sedoheptulose 7-phosphate, and E4P. The first two end products are associated with the biosynthesis of nucleotides and gram-negative bacterial lipopolysaccharides, respectively, while E4P is a precursor to the aromatic amino acids: phenylalanine, tyrosine, and tryptophan.

The initial siphoning of intermediates from glycolysis by the pentose phosphate pathway involves transketolase catalyzed transfer of a ketol group from D-fructose 6-phosphate to D-glyceraldehyde 3-phosphate to form E4P and D-xylulose 5-phosphate. Pentose phosphate epimerase then converts the D-xylulose 5-phosphate into D-ribulose 5-phosphate followed by pentose phosphate isomerase mediated transformation of the D-ribulose 5-phosphate into D-ribose 5-phosphate.

At this stage, the D-ribose 5-phosphate can be exploited by transketolase as an acceptor of a ketol group derived from another a molecule of D-fructose 6-phosphate forming a second molecule of E4P and D-sedoheptulose 7-phosphate. Finally, the enzyme transaldolase catalyzes transfer of a dihydroxyacetone group from the D-sedoheptulose 7-phosphate to D-glyceraldehyde 3-phosphate yielding the third molecule of E4P and D-fructose 6-phosphate. Thus, the nonoxidative pentose phosphate pathway achieves net conversion of two molecules of D-fructose 6-phosphate into three molecules of E4P.

The condensation of PEP and E4P is catalyzed by the enzyme DAHP synthase. Many microorganisms, including *E. coli*, produce three DAHP synthase isoenzymes: phenylalanine-sensitive DAHP synthase (phe), tyrosine-sensitive DAHP synthase (tyr), and tryptophan-sensitive DAHP synthase (trp). The tetrameric DAHP synthase (phe) has a subunit molecular weight of 35,000. The dimeric DAHP synthase (tyr) and DAHP synthase (trp) have subunit molecular weights approaching 40,000. The native forms of the enzymes are probably protein-PEP adducts. In *E. coli* the structural genes for DAHP synthase (tyr), DAHP synthase (phe), and DAHP synthase (trp) are aroF, aroG, and aroH, respectively. These genes are located at 56, 17, and 37 min, respectively, on the E. coli linkage map.

In wild-type E. coli, 80% of the total DAHP synthase activity is contributed by the phenylalanine-sensitive isoenzyme, while 20% is contributed by the tyrosine-sensitive isoenzyme. There are only traces of the DAHP synthase (trp) in E. coli.

After the condensation of PEP and E4P, the next reaction of the common aromatic pathway is an intramolecular exchange of the DAHP ring oxygen with C-7, accompanied by an oxidation at C-6 and a reduction at C-2. Cleavage of the phosphoester provides the driving force to form 3-dehydroquinate (DAH). This reaction is catalyzed by dehydroquinate synthase (DAH synthase).

Pure DAH synthase is a single polypeptide chain having a molecular weight of 40,000–44,000. The enzyme requires Co and NAD for activity, the latter in catalytic amounts. The formation of 3-dehydroquinate from DAHP is stereospecific and proceeds with inversion at the C-7 of DAHP without exchange of hydrogen with the growth medium.

Quinoid organics are formed from pathways which branch from the common aromatic and utilize DAH. A stereospecific syn-dehydration of 3-dehydroquinate introduces the first double bond of the aromatic ring system to yield 3-dehydroshikimate. The reaction is catalyzed by 3-dehydroquinate dehydratase. Schiff base formation between enzyme and substrate causes a conformational change in the substrate (twisted boat) that leads to the stereospecific course of the reaction.

Shikimate biosynthesis from 3-dehydroshikimate is catalyzed by shikimate dehydrogenase. This NADP-specific enzyme facilitates the hydrogen transfer from the A-side of NADPH.

Shikimate is phosphorylated to shikimate 3-phosphate by shikimate kinase. Shikimate kinase is a polypeptide of 10,000 daltons that is complexed with the bifunctional DAHP synthase-chorismate mutase. The kinase, only active in the complex, has been purified to homogeneity. Since the enzyme is inhibited by chorismate, prephenate, ADP, and 5-enolpyruvoylshikimate 3-phosphate are derepressed by growth on limiting tyrosine, shikimate kinase is believed to represent a key allosteric control point of the pathway in some types of host cells.

Shikimate-3-phosphate reacts with PEP to form 5-enolpyruvoyl shikimate 3-phosphate and inorganic phosphate. The reversible enzyme-catalyzed reaction is a transfer of an unchanged enolpyruvoyl moiety of PEP. Protonation of C-3 of PEP combined with a nucleophilic attack of the 5-hydroxyl of shikimate leads to a presumed intermediate from which 5-enolpyruvoylshikimate 3-phosphate is obtained in a 1,2-elimination of orthophosphate. The reaction is catalyzed by 5-enolpyruvoylshikimate 3-phosphate synthase.

The second double bond in the aromatic ring system is introduced through a trans-1,4-elimination of orthophosphate from 5-enolpyruvoyl shikimate 3-phosphate to yield chorismate. The reaction is catalyzed by chorismate synthase.

From chorismate, the endpoint of the common aromatic pathway, biosynthesis of a diverse number of aromatic compounds is possible. For example, as indicated in FIG. 4, the aromatic amino acids tryptophan, tyrosine, and phenylalanine can be synthesized from chorismate along their respective biosynthetic pathways. As previously noted, other commercially important aromatic compounds also produced from chorismate include folates, aspartame, melanin, prephenic acid, and indigo.

In addition to the common aromatic pathway, other pathways utilizing DAHP produce other aromatic metabolites. For example, catechol and quinoid organics, such as quinic acid, benzoquinone and hydroquinone, can be produced from pathways branching from the common aromatic pathway.

According to theoretical analyses, the maximum yield of DAHP and aromatic amino acids from glucose can be increased by two-fold if pyruvate is recycled back to PEP. The maximum yield may be calculated by assuming that the branched pathways are blocked and that the carbon flow is directed by the most efficient pathways with minimum loss to carbon dioxide and other metabolites. Under these conditions and under steady state conditions, the relative flux through each step can be calculated by balancing the input and output fluxes from each metabolite pool.

Figure 3A:
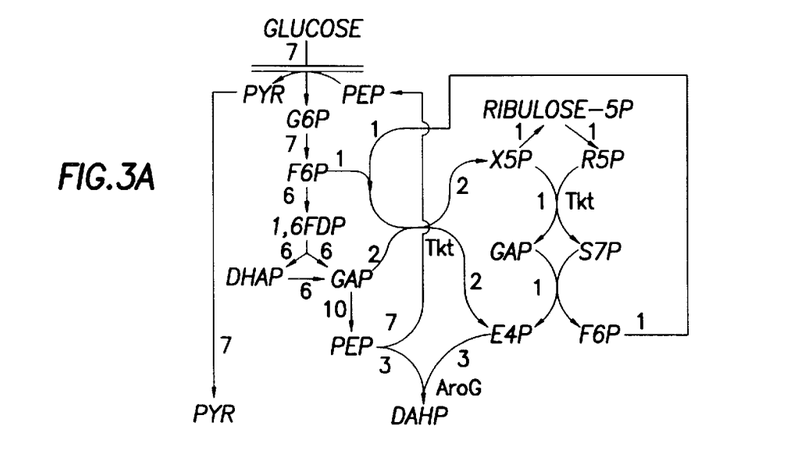
FIGS. 3A–3B. The reaction pathways for maximal conversion of glucose to DAHP for (A) strains without Pps, (B) strains overexpressing Pps. The numbers are the relative fluxes needed for converting 7 moles of glucose to DAHP. The abbreviations are: G6P, glucose 6-P; F6P, fructose 6-P; 1,6FDP, 1,6-fructose diphosphate; DHAP, dihydroxyacetone phosphate; GAP, glyceraldehyde 3-P, R5P, ribose 5-P; X5P, xylulose 5-P; S7P, sedoheptulose 7-P.

As shown in FIG. 3A, for maximum yield of DAHP production by strains without Pps overproduction, 7 moles of glucose are needed to produce 3 moles of DAHP (43% molar yield) and 7 moles of pyruvate which is further metabolized. The relative flux through each intermediate step is also shown in FIG. 3A. The formation of pyruvate is necessary because of the stoichiometry of the phosphotransferase system for glucose uptake.

In the presence of glucose, pyruvate is not recycled back to PEP efficiently because the enzyme Pps is not induced. The inventor has found that pyruvate is effectively recycled to PEP via overexpressed Pps, even in the presence of glucose, resulting in a two-fold increase in DAPH which approaches, if not achieves, the theoretical levels for DAHP synthesis.

Figure 3B:
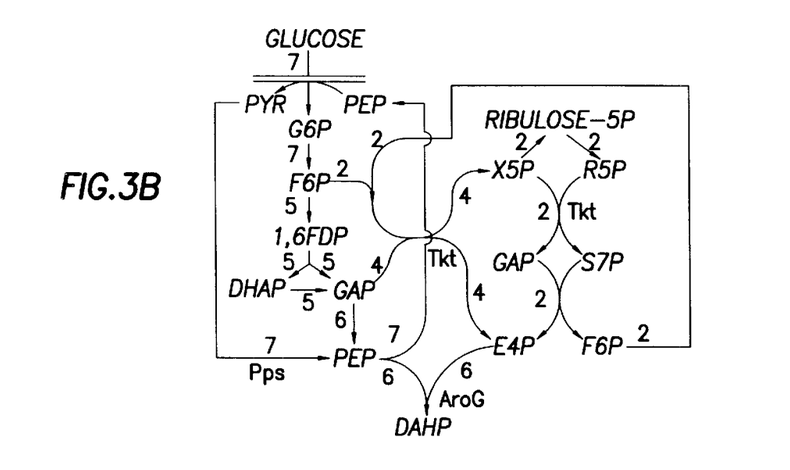

As shown in FIG. 3B, at the theoretical maximum, 6 moles of DAHP can be produced from 7 moles of glucose (86% molar yield). The nonoxidative part of the pentose pathway provides E4P, while overexpression of Pps recycles pyruvate back to PEP.

The data described above and shown in FIGS. 3A and 3B are in agreement with this flux distribution model. Controls with inactive Pps and with no Pps demonstrate that enhanced activity, through overexpression of Pps, is required to achieve high yields of DAHP and, of course, DAHP metabolites including metabolites of the common aromatic pathway.

In previous work, the inventor demonstrated that overexpression of Pps in host cells cultured on nutrient rich, glucose containing medium led to growth inhibition, increased glucose consumption, and excretion of pyruvate and acetate. Their previous study also showed that the effects of Pps overexpression on DAHP production, in actively growing cultures, are not as significant, and that the adverse effects of Pps overexpression on cell growth negated any beneficial effects on DAHP production.

The stimulation of glucose consumption in the previous work was attributed to the altered PEP/pyruvate ratio. It was hypothesized that increased PEP/pyruvate ratio stimulates the phosphotransferase system for increased glucose consumption, which in turn results in the excretion of pyruvate.

The inventor discovered that the problem of growth impairment could be overcome through the use of high density re-suspension cultures grown in nutrient lean, glucose media. Such re-suspension cultures attain high metabolic activity with low growth rates. This discovery led to DAHP yields approaching theoretical values.

In the present invention, PEP was redirected to the aromatic pathway, and thus the PEP/pyruvate ratio was decreased. This flux redirection explains the insensitivity of the specific glucose consumption rate to Pps overexpression in the experimental system of the present invention. The increased DAHP production from glucose caused by Pps overexpression also suggests that Pps actually functions in its physiological direction (from pyruvate to PEP) in vivo, even under glycolytic conditions.

PEP is also a precursor to the pathways that utilize the enzyme phosphoenol pyruvate carboxylase (Ppc) coded by the ppc gene. It has been reported that the deletion of ppc increased the production of phenylalanine and acetate. Moreover, it has been shown that the overexpression of Ppc in a wild-type host reduces acetate production. Both results may indicate that the flux through Ppc (from PEP to OAA) is reasonably significant under those conditions, and thus, the modulation of Ppc expression level may affect the utilization of PEP. However, in the present invention, deleting the chromosomal ppc gene did not have a positive effect on DAHP production, suggesting that the flux through Ppc is not important in the methods of the present invention.

One preferred embodiment of the present invention encompasses modification of a host cell to cause overexpression of an enzyme having the catalytic properties of naturally derived Pps, and, thereby maximizing the yield of DAHP to near theoretical yields. Enzymes having the catalytic activity of Pps include, but are not limited to, Pps produced by expression in whole cells of a naturally derived pps gene, enzymes produced by expression in whole cells of a naturally derived pps gene modified by sequence deletion or addition so that the expressed enzyme has an amino acid sequence that varies from unmodified Pps, abzymes produced to have catalytic sites with steric and electronic properties corresponding to catalytic sites of Pps, or other proteins produced to have the capability of catalyzing the conversion of pyruvate to PEP by any other art recognized means.

Figure 2A:
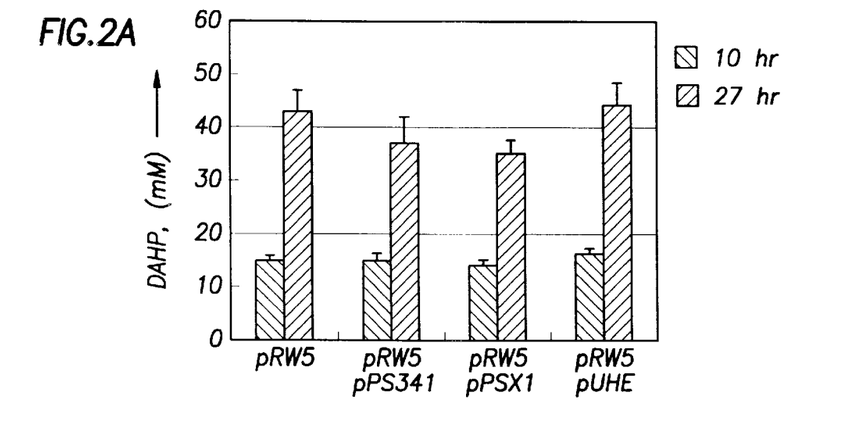
FIGS. 2A–2B. DAHP production at 10 and 27 hours after re-suspension. (A) Strain AB2847 with plasmids labeled in the abscissa. pPSX1 and pUHE denote pPS341X1 and pUHE23-2, respectively. (B) Strains AB2847 (labeled as AB), JCL1283 ppc::Km (labeled as ppc), and JCL1362 pps::MudK (labeled as pps) with plasmids labeled in the abscissa.

In another preferred embodiment, the inventor has observed that the Pps effect on DAHP production is enhanced by the simultaneous overexpression of Tkt. Such simultaneous overexpression ensures that both precursors necessary for DAHP biosynthesis are overproduced. Although simultaneous overexpression of Pps and Tkt may be required to attain near theoretical yields of DAHP, the overexpression of Pps alone in the methods of the present invention significantly enhanced DAHP production over Tkt overexpression alone (FIG. 2A). This result may suggest that without pyruvate recycling mediated by Pps (FIG. 3A), sufficient PEP flux to DAHP synthesis cannot be achieved.

Additionally, the transformation of DNA, including the pps gene, into microorganisms engineered for the overexpression of other substrates, and/or overexpression or derepression of enzymes in the pentose phosphate or common aromatic pathway can be used to tailor the microorganism to achieve near theoretical yields of such DAHP metabolites as tyrosine, tryptophan, phenylalanine, and other aromatic metabolites such as indigo, catechol and quinoid organics such as quinic acid, benzoquinone, and hydroquinone.

Enzymes catalyzing reactions in the pentose phosphate or common aromatic pathway include those enzymes produced by expression in whole cells of naturally derived pentose phosphate or common aromatic pathway genes, enzymes produced by expression of naturally derived pentose phosphate or common aromatic pathway genes that have been modified by sequence deletion or addition so that the expressed enzyme has an amino acid sequence that differs from the natural enzyme, or abzymes having catalytic sites with steric and electronic properties corresponding to catalytic sites of a natural enzyme in the common aromatic or pentose phosphate pathway.

Pps or enzymes having Pps-like catalytic activity can be overexpressed relative to Pps production in wild type cells (as measured by standard PEP synthase activity assays known in the art and described in Example 1) in conjunction with any number of other enzymes in the common aromatic pathway or pathways branching therefrom. For example, overexpression of Pps, DAHP synthase, and transketolase; Pps, DHQ synthase, and transketolase; Pps, DAHP synthase, DHQ synthase, and transketolase; Pps, transketolase, and shikimate kinase; Pps, transketolase (Tkt), and chorismate mutase; or any other common aromatic pathway enzymes in conjunction with Pps overproduction can enhance carbon source input to and/or throughput of the common aromatic pathway.

Enhanced expression of genes coding for proteins able to perform or control pentose phosphate or common aromatic pathway enzymatic functions is mediated by genetic elements transferable into a host cell. Genetic elements as herein defined include nucleic acids (generally DNA or RNA) having expressible coding sequences for products such as proteins, apoproteins, or antisense RNA, which can perform or control pentose phosphate or common aromatic pathway enzymatic functions. The expressed proteins can function as enzymes, as repressor or derepressor agents, or to control enzyme expression.

The nucleic acids coding these expressible sequences can be either chromosomal (e.g., integrated into a host cell chromosome by homologous recombination) or extrachromosomal (e.g., carried by plasmids, cosmids, etc.). In addition, genetic elements are defined to include optional expression control sequences including promotors, repressors, and enhancers that act to control expression or derepression of coding sequences for proteins, apoproteins, or antisense RNA. For example, such control sequences can be inserted into wild type host cells to promote overexpression of selected enzymes already encoded in the host cell genome, or alternatively can be used to control synthesis of extrachromosomally encoded enzymes.

The genetic elements of the present invention can be introduced into a host cell by vectors including, but not limited to, plasmids, cosmids, phages, Yeast artificial chromosomes or other vectors that mediate transfer of the genetic elements into a host cell, or mixtures thereof. These vectors can include an origin of replication along with cis-acting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin.

A preferred means for introducing genetic elements into a host cell utilizes an extrachromosomal multi-copy plasmid vector into which genetic elements in accordance with the present invention have been inserted. Plasmid borne introduction of the genetic element into host cells involves an initial cleaving of a plasmid with a restriction enzyme, followed by ligation of the plasmid and genetic elements in accordance with the invention. Upon recircularization of the ligated recombinant plasmid, transformation or other mechanisms for plasmid transfer (e.g., electroporation, microinjection, etc.) is utilized to transfer the plasmid into the host cell.

Plasmids suitable for insertion of genetic elements into the host cell include, but are not limited to, pBR322 and its derivatives such as pAT153, pXf3, pBR325, and PBR327, pUC vectors, pACYC and its derivatives, pSC101 and its derivatives, and ColEl. U.S. Pat. No. 5,168,056, incorporated herein by reference, teaches the incorporation of the tkt gene which codes for the enzyme Tkt into host cell. Tkt catalyzes the conversion of the carbon source D-fructose-6-phosphate to E4P, one DAHP precursor.

Suitable host cells for use in the present invention are members of those genera capable of being utilized for industrial biosynthetic production of desired aromatic compounds. Accordingly, host cells can include prokaryotes belonging to the genera Escherichia, Corynebacterium, Brevibacterium, Arthrobacter, Bacillus, Pseudomonas, Streptomyces, Staphylococcus, or Serratia. Eukaryotic host cells can also be utilized, with yeasts of the genus Saccharomyces or Schizosaccharomyces being preferred.

More specifically, prokaryotic host cells suitable for use in the present invention include, but are not limited to, *Escherichia coli, Corynebacterium glutamicum, Corynebacterium herculis, Brevibacterium divaricatum, Brevibacterium lactofermentum, Brevibacterium flavum, Bacillus brevis, Bacillus cereus, Bacillus circulans, Bacillus coagulans, Bacillus lichenformis, Bacillus megaterium, Bacillus mesentericus, Bacillus pumilis, Bacillus subtilis, Pseudomonas aeruginosa, Pseudomonas angulata, Pseudomonas fluorescens, Pseudomonas tabaci, Streptomyces aureofaciens, Streptomyces avermitilis, Streptomyces coelicolor, Streptomyces griseus, Streptomyces kasugensis, Streptomyces lavendulae, Streptomyces lipmanii, Streptomyces lividans, Staphylococcus epidermis, Staphylococcus saprophyticus,* or *Serratia marcescens* and their genetically engineered strains or mixtures thereof. Preferred eukaryotic host cells include *Saccharomyces cerevisiae* or *Saccharomyces carlsbergensis* and their genetically engineered strains or mixtures thereof.

For industrial production of primary metabolites derived from chorismate (such as aromatic amino acids), deregulated mutant strains of the above recited species that lack feedback inhibition of one or more enzymes in the metabolic biosynthetic pathway are preferred. Such strains can be created by random or directed mutagenesis, or are commercially available. Examples of *E. coli* strains having DAHP synthase, prephenate dehydratase, or chorismate mutase feedback inhibition removed are described in U.S. Pat. No. 4,681,852 to Tribe and U.S. Pat. No. 4,753,883 to Backman et al., incorporated herein by reference.

To overcome the stoichiometric limitations in the condensation of E4P and PEP, the present invention overexpresses Pps in the presence of glucose and directs more carbon flux into the production of DAHP.

The following list of abbreviations for compounds commonly noted in the specification and Examples is presented as follows:

| | |
|---|---|
| DHQ | 3-dehydroquinate |
| DAH | 3-deoxy-D-arabino-heptulosonic acid |
| DAHP | 3-deoxy-D-arabino-heptulosonic acid 7-phosphate |
| TSP | 3-(trimethylsilyl)propionic-2,2,3,3-d sub 4 acid, sodium salt |
| PEP | Phosphoenol pyruvate |
| NADH | beta -nicotinamide adenine dinucleotide phosphate, reduced form |
| Kan | kanamycin |
| Ap | ampicillin |
| Tc | tetracycline |
| Cm | chloramphenicol |
| Pps | phosphoenolpyruvate synthase |
| Tkt | transketolase |

Strains and Plasmids

*Escherichia coli* AB2847 aroB mal T6$^r$, obtained from *E. coli* Genetic Stock Center, Yale University, was used as the preferred host strain for DAHP production. BJ502 tkt-2 fhuA22 garB10 ompF627 fadL701 relA1 pit-10 spoT1 mcrB1 phoM510, also from *E. coli* Genetic Stock Center, was used in the identification of the tkt clone. JCL1242 ppc::Km was constructed as described previously by inserting a kanamycin cassette into a cloned ppc gene, which is then integrated into the chromosome by homologous recombination.

Plasmid pPS341 was constructed by cloning a fragment of *E. coli* chromosomal DNA containing pps gene into an IPTG-inducible expression vector pUHE23-2 (a pBR322 derivative) as taught by Patnaik et al., (Patnaik, R., W. D. Roof, R. F. Young, and J. C. Liao, "Stimulation of Glucose Catabolism in *Escherichia coli* by a Potential Futile Cycle," *J. Bacteriology* 1992, 174: 7527–7532) and the contents of which are herein incorporated by reference. Plasmid pPS341X1 containing the inactive gene product of pps was constructed by codon insertion mutagenesis, the details of which are fully described in Patnaik et al. (Castilho, B. A., P. Olfson, and M. J. Casadaban, "Plasmid Insertion Mutagenesis and lac Gene Fusion with Mini-Mu Bacteriophage Transposons," *J. Bacteriology.* 1984, 158: 488–495). The pps gene on pPS341 was inserted with a Mu dII1734 lac$^+$ Km$^r$ (MudK) according to published protocol of Castiho et al., the contents of which are herein incorporated by reference. Briefly, a Mu lysate was made from a donor strain POII1734/pPS341, which was lysogenized by the mini-Mu element and a Mu cts. The lysate was used to infect a Mu lysogen of HG4 pps pck, and colonies were selected for Ap$^r$ and Km$^r$ simultaneously to ensure that the mini-Mu element hopped to the plasmid. Colonies were further screened for Pps$^-$ phenotype (inability to grow on pyruvate). Restriction analysis of plasmid DNA further confirmed the insertion of the MudK element into the pps gene on plasmid pPS341. 20% of these selected colonies showed IPTG-dependent expression of β-galactosidase, indicating an in-frame insertion. The plasmid from one such colony was named pPS1734, which was then linearized at the ScaI site, and transformed into strain JC7623 recB21 recC22 sbcB15. Transformants were selected for Km$^r$ and scored for Ap sensitivity. Such colonies presumably contained pps::MudK on the chromosome. By use of P1 transduction, this locus was moved to AB2847 and Km$^r$ transductants were further screened for inability to grow on pyruvate. One such colony was designated JCL1362 and used for later studies. The MudK insertion into chromosomal pps was further confirmed by cotransduction frequency (89%) with Tet$^r$ marker from strain CAG12151 zdh-925::Tn10.

Plasmid pRW5, Genencor International, South San Francisco, Calif., is a pACYC derivative and contains aroG-$^{fbr}$. This plasmid also contains a lacI gene, and the aroG$^{fbr}$ is expressed from a lac promoter. To construct plasmid pAT1 containing both aroG$^{fbr}$ and tktA, a 5-Kb BamH1 fragment of *E. coli* DNA was cut from page 473 of the Kohara miniset (National Institute of Genetics, Japan), and was inserted into the BamH1 site of pRW5. This fragment was reported to contain the tktA gene, and was confirmed by its ability to complement a tkt strain (BJ502) for growth on ribose, and also from the migration distance of the gene product as judged on a 12% SDS-PAGE (molecular weight ca. 72,500). Construction of pPS706 and the control The plasmid pPS706 was constructed by inserting a 2.4 kb PCR fragment containing the promoter-less pps gene into the vector pJF118EH. The primers were designed from the published pps sequence and contained an EcoRI site and a φ10 ribosome binding site upstream of the pps sequence and a BamHI site downstream of the sequence. The PCR product was then cloned into the EcoRI and BamHI sites of pJF118EH. Positive clones were selected based on complementation of HG4 pps for growth on pyruvate. Expression of pps from this construct is controlled by the tac promoter inducible by IPTG.

Figure 5:
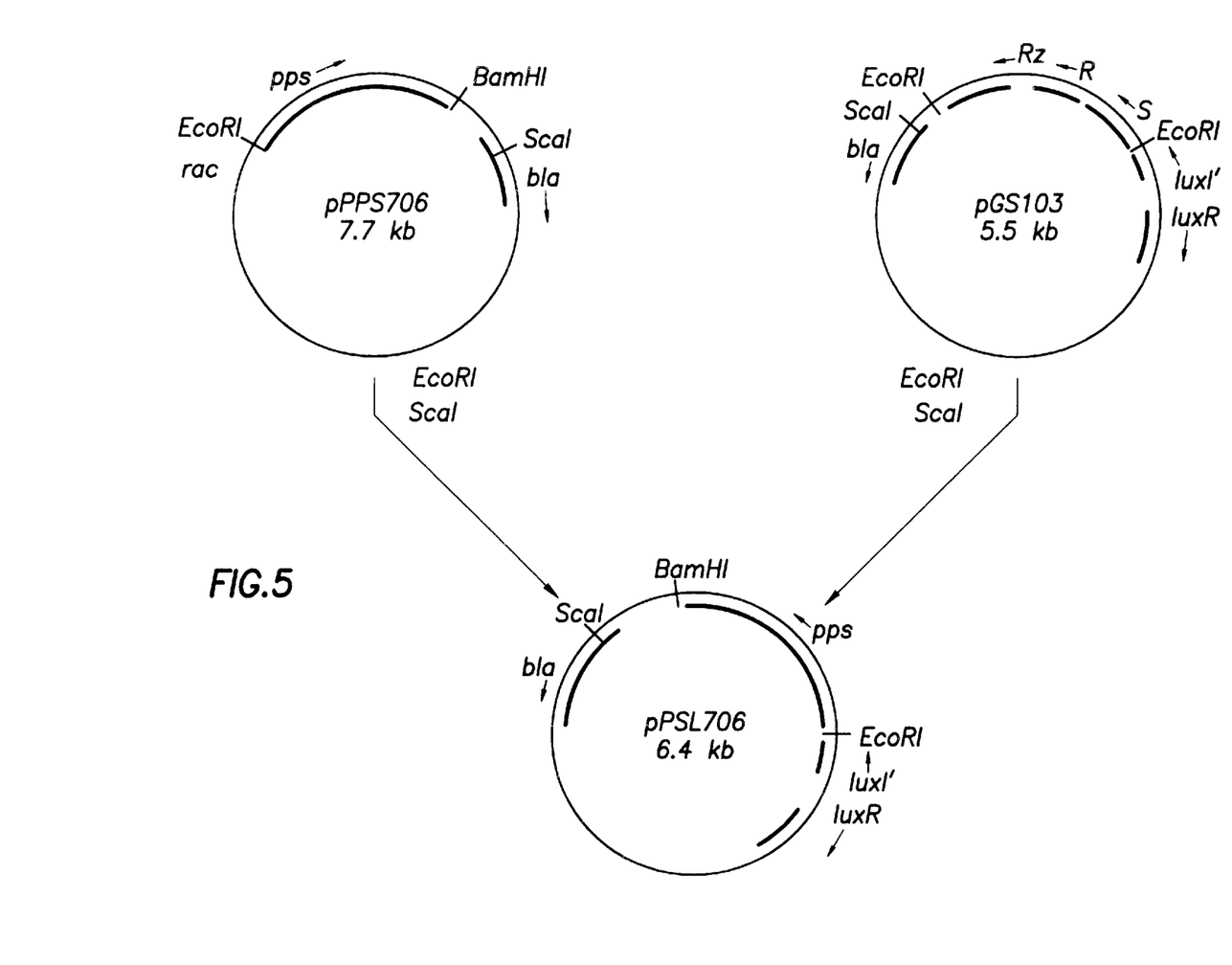
FIG. 5. The construction of pPSL706. Plasmids pPS706 and pGS103 were restricted with EcoRI and ScaI. The fragments containing pps from pPS706 and the fragment containing luxI' were purified and ligated to generate pPSL706. Plasmid pPS706 was constructed by inserting a pps PCR fragment into 9 the cloning vector pJF118EH.
Figure 6A:
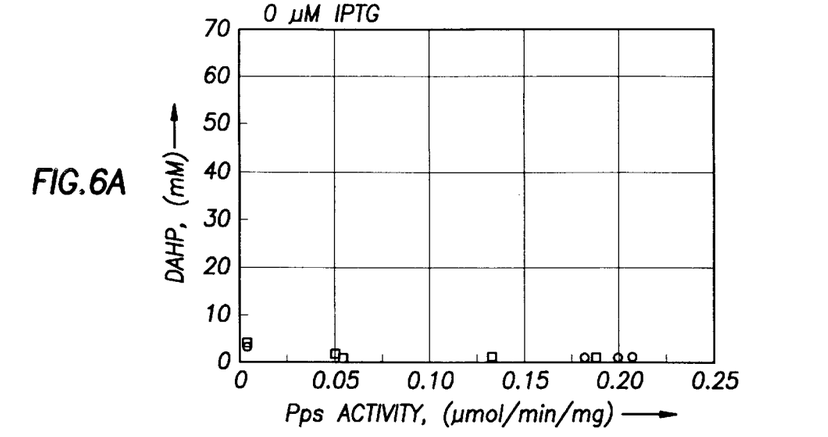
FIGS. 6A–6F. Effects of Pps activity on DAHP production from glucose at different IPTG and autoinducer concentrations. The strains are AB2847/pPSL706/pAT1 and AB2847/pPSL706/pRW5. Plasmid pGS 104 was used to substitute pPSL706 as a control, and the data are the leftmost point in each graph.
Figure 6B:
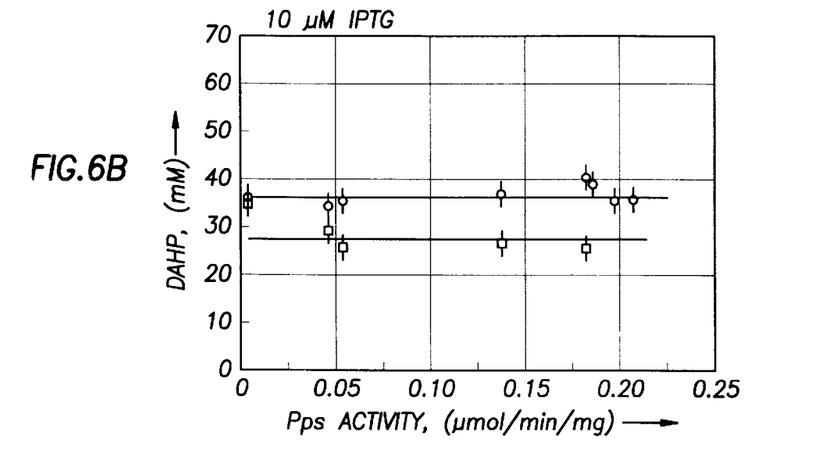
Figure 6C:
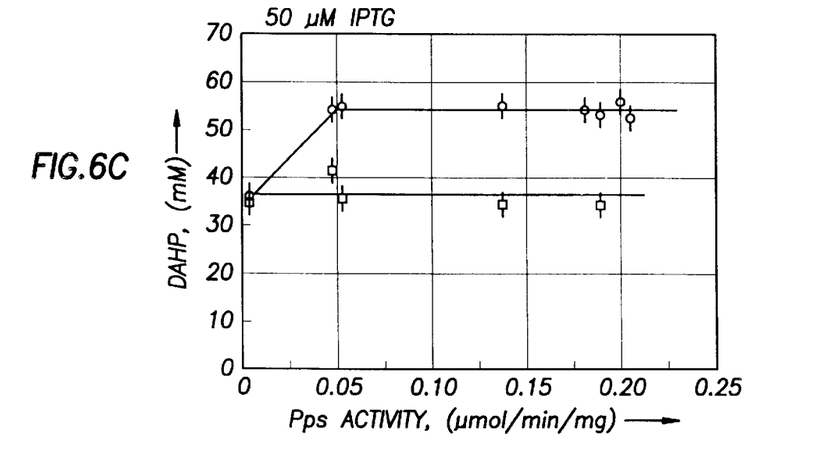
Figure 6D:
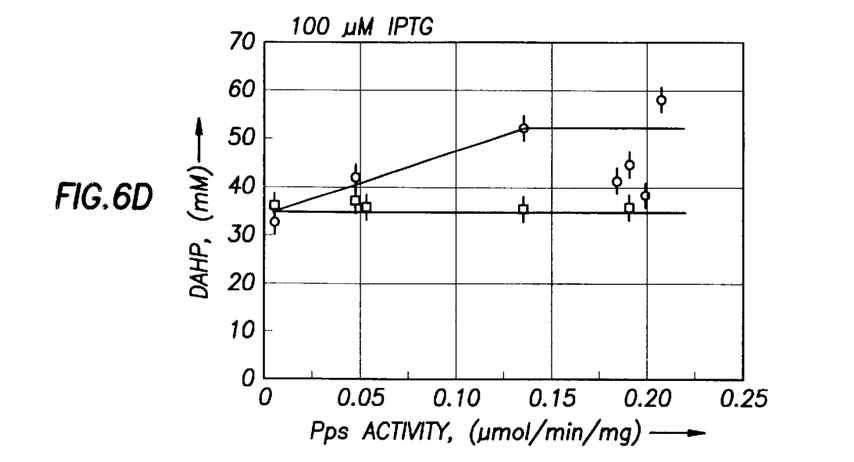
Figure 6E:
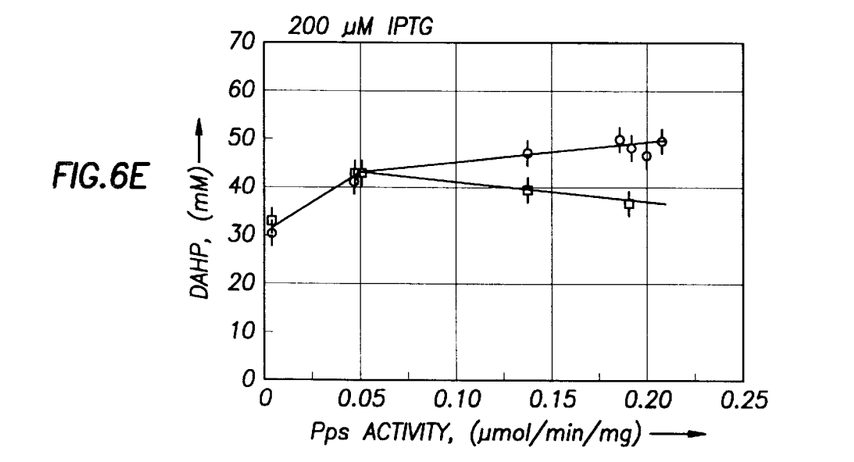
Figure 6F:
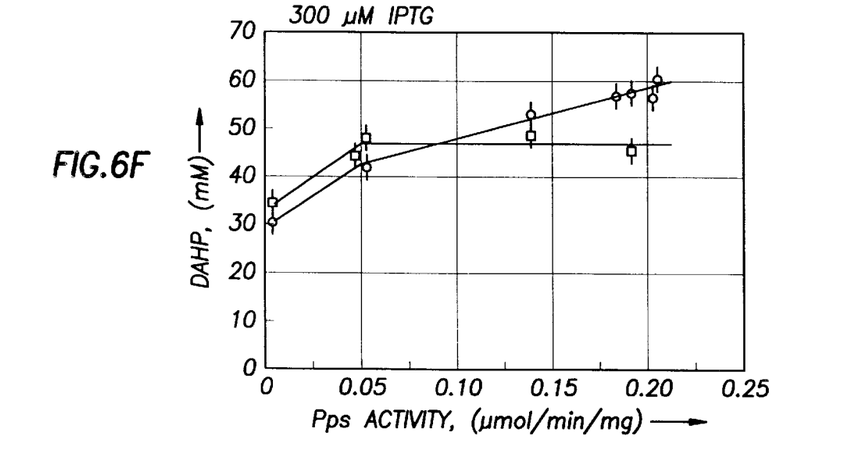

The plasmid pPSL706 was then constructed from pPS706 as shown in FIG. 5. Briefly, a ScaI/EcoRI fragment containing the pps gene was cut from pPS706 and purified from the restriction buffer. This fragment was then cloned into a purified ScaI-EcoRI fragment containing the luxI' promoter from pGS103, kindly given to the inventor by Tom Baldwin. Department of Biochemistry and Biophysics, Texas A&M University. Expression using this system is controlled by the autoinducer (AI) in the culture media. pPSL706 is ampicillin resistant and compatible with other pACYC184 derivatives such as pRW5 and pATI. The strains and plasmids used are summarized in Table I and Table II.

TABLE I

Bacterial Strains

| Strain | Relevant genotype | Source |
|---|---|---|
| AB2847 | aroB mal T6$^r$ | Genetic Stock Center |
| BJ502 | tkt-2 | Genetic Stock Center |
| JC7623 | recB2l recC22 sbcB15 | (26) |
| HG4 | pck-2 pps-3 | Hughes Goldie |
| POII1734 | araD139 ara::(Mu cts)3 Δ(lac)X74 gal U galK rpsL with Mu dII1734 lac + (Km$^r$) | (4) |
| CAG12151 | zdh-925::TnlO | (22) |
| JCL1242 | VJS676 but ppc::Km | (5) |
| JCL1283 | AB2847 but ppc::Km | This study |
| JCL1362 | AB2847 but pps::Mu dII1734 | This study |

TABLE II

Plasmids

| Plasmids | Relevant genotype | Source |
|---|---|---|
| pUHE23-2 | Ap$^r$; IPTG-inducible T7(A1) early promoter | H. Bujard |
| pPS341 | same as pUHE23-2 but pps$^+$ | (18) |
| pPS341X1 | same as pPS341 but pps-50 (2-codon insertion) | (18) |
| pPS1734 | pPS341::Mu dII1734 (Km$^r$ lac$^+$) | This study |
| pRW5 | pACYC184 derivative Cm$^r$, but tandem lac promoters aroG$^{fbr+}$ | Genencor International |
| pAT1 | same as pRW5 but tktA$^+$ | This study |
| pPS706 | as pJF118EH but pps$^+$ | This study |
| pPSL706 | as pGS104 but pps$^+$ | This study |

Media and growth conditions

All cloning procedures were carried out in Luria-Bertani medium. YE medium contained $K_2HPO_4$ (14 g/L), $KH_2PO_4$ (16 g/L), $(NH_4)_2SO_4$ (5 g/L), $MgSO_4$ (1 g/L), yeast extract (15 g/L), and D-glucose (15 g/L). Minimal medium used for high-cell density re-suspension cultures contains per liter, $K_2HPO_4$ (14 g), $KH_2PO_4$ (16 g), $(NH_4)_2SO_4$ (5 g), $MgSO_4$ (1 g), D-glucose (15 g) and was also supplemented with thiamine (1 mg), shikimic acid (50 mg), L-tyrosine (8 mg), L-phenylalanine (8 mg), and L-tryptophan (4 mg). The minimal medium was supplemented with succinate (0.1 g/L) when growing the ppc mutant and its control. For stable maintenance of plasmids, ampicillin (100 mg/ml), chloramphenicol (50 mg/ml) were added to the culture medium. Concentrations of the antibiotics were reduced by half when minimal medium was used.

Overnight cultures in YE medium were grown at 37° C. in a roller drum and then were subcultured in the same medium with appropriate enablement. Cultures were grown in 250 ml shake flasks at 37° C. in a gyratory water bath shaken at 200 rpm. After four hours of incubation ($OD_{550}$: 2–3) cultures were induced with isopropyl-β-D-thiogalactopyranoside, IPTG (1 mM). Cells were harvested from late stationary phase by centrifugation at 6000×G and were washed twice with minimal medium before re-suspending in the same minimal medium supplemented with appropriate enablement and IPTG (1 mM). Initial $OD_{550}$ of all high-density re-suspension cultures were about 4.0. The optical density can be greater than 4.0. In other terms, the media may contain at least $5 \times 10^9$ cells/mL. Samples from the re-suspension cultures were withdrawn periodically for assaying DAH(P) and glucose concentration in the medium.

Determination of glucose and DAHP

Cells were removed from samples by centrifugation and the supernatants were stored at 4° C. until all samples had been collected. Residual glucose in the culture supernatant was determined by the dinitrosalicylic acid assay for total reducing sugars. For additional information an this assay, see Miller (Miller, G. L. 1958. Use of dinitrosalicylic acid reagent for determination of reducing sugars. Anal. Chem. 31:426–428) and Patnaik et al. (Patnaik, R., W. D. Roof, R. F. Young, and J. C. Liao. 1992. Stimulation of glucose catabolism in Escherichia coli by a potential futile cycle. J. Bacteriol. 174:7527–7532), the contents of which are herein incorporated by reference. The concentration of DAH(P) in the supernatant was determined by the thiobarbiturate assay. For additional information on this assay, see Draths et al. and Gollub et al. (Gollub, E., H. Zalkin, and D. B. Sprinson. 1971. Assay for 3-Deoxy D-arabino-heptulosonic Acid 7-phosphate Synthase. Methods in Enzymology 17A:349–350), the contents of which are herein incorporated by reference. This assay does not distinguish between DAH and DAHP.

Enzyme assays

Cells were harvested by centrifugation at 6000×G and were washed and re-suspended in potassium phosphate buffer (50 mM) pH 7 or 5 mM Tris-Cl-1 mM $MgCl_2$ (pH 7.4), for DAHP synthase or PEP synthase (Pps) assay, respectively. Cell extracts were prepared by rupturing cells through a French pressure cell (SLM Aminco, Urbana, Ill.) at 160,000 lb/in$^2$. DAHP synthase activity was assayed by the procedure of Schoner as described more fully in Schoner et al. (Schoner, R. and K. M. Herrmann. 1976. 3-Deoxy-D-arabino-heptulosonate 7-phosphate Synthase. J. Biol. Chem. 251:5440–5447), the contents of which are herein incorporated by reference. Pps activity was assayed as described previously. Total protein in the extracts was determined with the Bio-Rad dye reagent (Bradford assay) with bovine serum albumin as the standard.

Effects on Pps on DAHP production from glucose

The purpose of constructing pPS706 was to express Pps with an inducible promoter not affected by IPTG. This plasmid, together with pRW5, provided a means to vary the activities of the enzymes, Pps and AroG, independently under the control of two different promoters. The third enzyme, TktA, was under the control of its natural promoter and thus variable in only an on/off mode (presence or absence of the gene). This system then allowed the examination of Pps effect over a wider range of conditions. Moreover, it is possible that this system would show an optimal point at which the enzyme activities were high enough to provide maximum production of DAHP but not so high as to exert a protein load on the system, thereby decreasing DAHP production. Therefore, DAHP production was measured by AB2847/pRW5/pPS706 and AB2847/pATI/pPS706 in a glucose medium at varying IPTG and autoinducer (N-(3-xox-hexanoyl)-hmoserine lactone) concentrations.

FIG. 6 shows the activity of Pps at various AI and IPTG concentrations in glucose medium. At low IPTG concentrations (low AroG activities), Pps has little or no effect on DAHP production. When IPTG concentration exceeded 50 mM, Pps effect began to show. Plasmid pGS 104, isogenic with pPS706 except for the pps locus, was used as a control, and it showed no effect with or without the addition of AI. The Pps effect was more significant in the strain overexpressing TktA, and it was not due to a variation in AroG or TktA activities, since AroG and TktA activities were shown to be constant with or without Pps overexpression. From the measurement of residual glucose (data not shown), the yields of DAHP from glucose reached 100%, which corresponds to 70–80% after adjusting for the overestimation of DAHP. The latter value is consistent with that predicted by the stoichiometric analysis, which indicates a maximum theoretical yield of 86% from glucose when pyruvate is recycled to PEP by Pps. Although increases in DAHP levels and yields with Pps activity were observed, a drop with higher Pps activity which would have provided a peak was not evident. The levels of DAHP instead seem to reach saturation with further induction of Pps.

Formation of byproducts

To gain insight into the metabolic flux distribution, the culture broth was analyzed for fermentation byproducts by use of HPLC. Samples were taken from cultures in glucose media with varying activities of Pps, AroG, and TktA. Results indicate that the host strain AB2847 produced acetate, succinate, and formate as the major byproducts when neither AroG nor Pps was overexpressed. Production of these acids generally decreased with the increase in IPTG concentration, except formate. This decrease correlates with the increase in DAHP production. When AB2847/pAT1/pPS706 was cultured in glucose with IPTG concentration beyond 50 mM, the broth had undetectable levels of these acids (data not shown). While levels of formic and acetic acid decreased with increase in Pps activity, succinic acid either remained constant (0 $\mu$M IPTG) or increased (10.50 $\mu$M IPTG) with an increase in Pps activity. This increase could be contributed to Pps induced increase in PEP level, which is spilled over through PEP carboxylase and eventually to succinate.

EXAMPLE 1

Production of DAHP

This example demonstrates that the *E. coli* AB2847 is unable to utilize DAHP, and accumulates DAHP in the medium if DAHP synthase is overexpressed. This strain was used as a host for detecting the flux committed to the aromatic pathways. Since Draths et al. (Draths, K. M., D. L. Pompliano, D. L. Conley, J. W. Frost, A. Berry, G. L. Disbrow, R. J. Staversky, and J. C. Lievense, "Biocatalytic synthesis of aromatics from D-glucose: The role of transketolase," *J. Am. Chem. Soc.*, 1992, 114, 3956–3962) have shown a possible limitation in the production of DAHP by E4P, pAT1 (containing both aroG$^{fbr}$ and tktA) was transformed into AB2847 to eliminate the limitation of E4P. To test whether PEP supply limits DAHP production, PEP synthase (Pps) was overexpressed in AB2847/pAT1 by transforming plasmid pPS341 into this strain. 20–70 copies of the pps gene were expressed in the host cells. As a control, pPS341 was substituted by pPS341X1, which encodes an inactive, but stable pps gene product. The use of the inactive Pps control allowed discrimination between the effect of Pps activity and that of protein overexpression. AB2847/pAT1/pUHE23-2 and AB2847/pAT1 were also used without any other plasmid as additional controls to identify the effect of the cloning vector, pUHE23-2, on DAHP production.

Figure 1A:
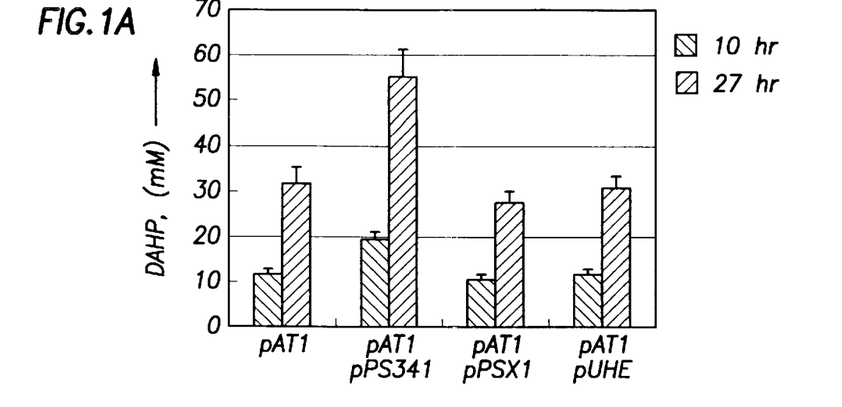
FIGS. 1A–1B. Overexpression of Pps increases the production of DAHP. The host strain used was AB2847 and the plasmids used are as labeled in the figure. Note that pPSX1 and pUHE denote pPS341X1 and pUHE23-2, respectively. These strains were cultured first in the YE medium (a rich medium) to late stationary phase, and then washed and re-suspended in a minimal medium. (A) DAHP concentrations measured at 10 and 27 hours after re-suspension. (B) The activities of DAHP synthase (aroG) and Pps measured at 27 hours after re-suspension.
Figure 1B:
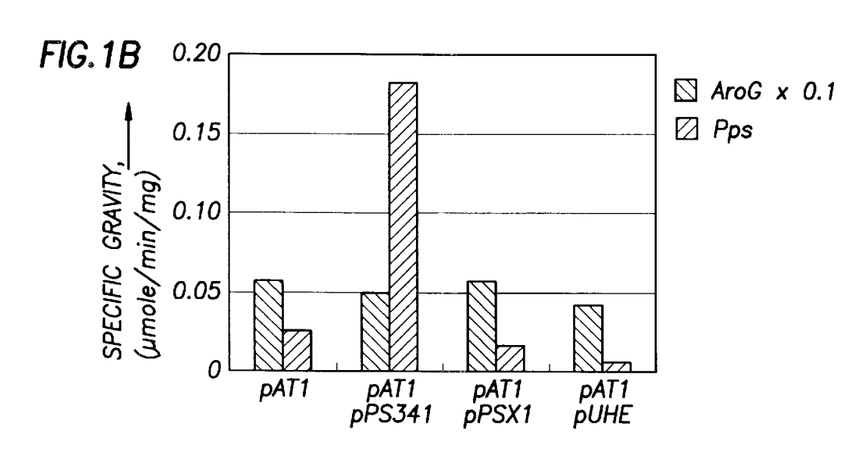

As described above, the strains were grown in a rich medium (YE) with IPTG and re-suspended in a minimal medium. Since the overexpression of Pps under glycolytic conditions may cause growth inhibition, re-suspension cultures were used to minimize the effect of cell growth on the biocatalytic conversion. After re-suspension, the excreted DAHP and residual glucose were measured periodically. At 27 hours after re-suspension, samples were taken for Pps and AroG assays. FIG. 1A shows that the strain overexpressing active Pps increased the DAHP production by almost two-fold. The strains containing pPS341X1 or pUHE23-2 produced the same amount of DAHP as the one containing only pAT1. FIG. 1B shows that, as expected, Pps activity was ten-fold overexpressed in the strain containing pPS341, while the aroG activity in all strains remain almost constant. These data strongly suggest that the activity of Pps is responsible for the increase in the DAHP production, whereas the inactive Pps or the cloning vector has no observable effect on DAHP production.

The specific glucose consumption rates of these strains were not influenced by the presence of active or inactive Pps, nor by the cloning vector (data not shown). Therefore, the strain overexpressing Pps showed almost a two-fold increase in overall DAHP yield (c.a. 90% molar) as compared to the controls (c.a. 52% molar), suggesting that Pps improves both the productivity and the yield of DAHP production. The maximum theoretical yield from glucose to DAHP is 86%, which is slightly lower than the measured yield from the strain overexpressing Pps. Because both glucose and DAHP measurements were reasonably reproducible, the discrepancy may be attributed to the inaccuracy of the extinction coefficient used to calculate DAHP concentration. However, the extinction coefficient has been calibrated by biosynthesized DAHP from cell extract and known amounts of E4P and PEP. Results show that the extinction coefficient is roughly within 30% accuracy. Therefore, the yield of DAHP is a reasonably close to the theoretical maximum, even though it may and probably is lower than the theoretical value.

To determine whether the Pps effect requires overexpressed transketolase (Tkt) as well, plasmid pRW5, which contains only aroG$^{fbr}$, was used in place of pAT1 in the above experiments. It was found that overproduction of Pps did not increase the DAHP production (FIG. 2A) without the elevated Tkt activity. Therefore, as limitation of small molecules in the biosynthesis of DAHP is concerned, the first limitation arises from the supply of E4P. This bottleneck shifts to the supply of PEP when Tkt is overexpressed, which is believed to increase the supply of E4P.

EXAMPLE 2

Figure 2B:
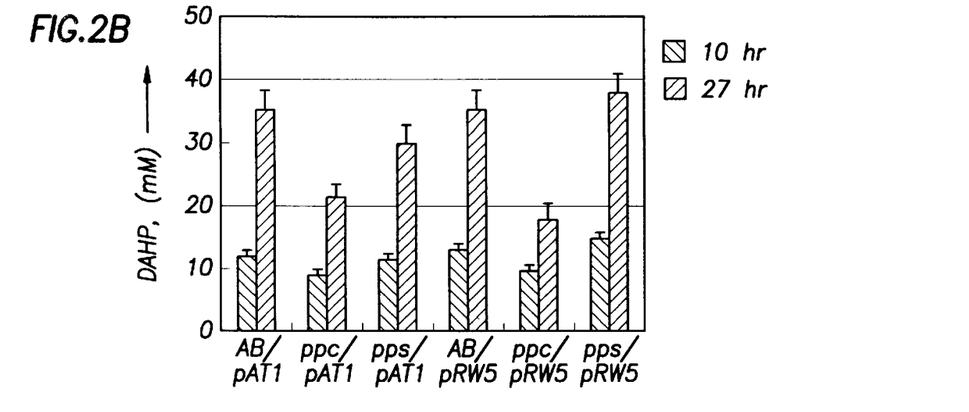

As shown above, Pps overexpression improved DAHP production from glucose. To determine whether the basal level of pps expression in glucose medium contributed to the production of DAHP, the chromosomal pps gene in strain AB2847 was knocked out. The resulting strain (JCL1362) was used as the host to repeat the above experiments. Results show that inactivation of chromosomal pps did not significantly affect the DAHP production in strains containing pRW5 or pAT1 (FIG. 2B). Therefore, the basal level of pps expression in glucose medium did not contribute to the DAHP production.

Since PEP is also converted to OAA by Ppc, the deletion of this enzyme may increase the supply of PEP. Therefore, the ppc gene on the chromosome of AB2847 was inactivated to determine whether DAHP production could be increased without Pps overexpression. This was done by transducing AB2847 with a P1 lysate grown on JCL1242 ppc::Km. The resulting transductant, JCL1283 aroB ppc::Km was then transformed with pAT1 or pRW5 and tested for DAHP production in the re-suspension culture as described above. To avoid limitation of OAA in the ppc strain, the culture medium was supplemented with succinate, which was shown to have no effect on DAHP production (data not shown). Contrary to the expectation, ppc mutation did not increase the production of DAHP (FIG. 2B), suggesting that the metabolic flux from PEP to OAA was not significant under the experimental conditions tested here. In fact, the ppc mutation actually decreased the DAHP production for unknown reasons.

EXAMPLE 3
Production of Tryptophan

Existing technologies for the production of tryptophan utilize either naturally occurring microorganisms, mutated microorganisms, or genetically engineered microorganisms. These microorganisms include, but are not limited to *Escherichia coli,* Brevibacteria, Corynebacteria, and yeast. The altered pathways may include: (1) deletion of pathways branching off to phenylalanine and tyrosine; (2) deletion of pyruvate kinases (pyk); (3) deletion of PEP carboxylase (ppc); (4) deletion of phosphoglucose isomerase (pgi); (5) desensitize feed-back inhibition of enzymes in the chorismate pathway and the trp operon; (6) deletion of the repressor, trpR, and the attenuation sequence in the trp operon; (7) deletion of tryptophan degradation enzymes; (8) overexpression of the trp operon enzymes; (9) overexpression of the wild-type or feedback resistant AroF, AroG, or AroH, or any enzyme in the chorismate pathway; (10) overexpression of SerA; and (11) overexpression of TktA or TktB.

To produce tryptophan, strain ATCC31743 which contains chromosomal markers such as trpR Δ(trpAE) tna can be used as a host. This strain also contains a plasmid pSC102trp which harbors trpAE operon. Plasmids pATI and pPS341 (or pPS706 or pPSL706) can be transformed into this strain. The serA gene can be cloned into any of the plasmids. Alternatively, these cloned genes (trpAE, aroG, tktt, pps or serA) can be consolidated to one or two plasmids. The resulting strain was grown in MT medium which contains, per liter: $KH_2PO_4$, 3 g; $K_2HPO_4$, 3 g; $K_2HPO_4$, 7 g; $NH_4CL$, 3 g; $MgSO_4$, 0.2 g; $FeSO_4$ ($7H_2O$), 10 mg; glucose, 0 to 30 g.

The Pps technology is compatible with all of the above alterations in metabolism. Alterations that favor the supply of E4P, such as the deletion of phosphoglucose isomerase, may eliminate the need for overexpression Tkt associated with Pps in the preferred embodiment. Higher AroG levels may also eliminate the need for overexpressing Tkt. The Pps technology can be used in microorganisms such as Brevibacteria and Corynebacteria.

EXAMPLE 4
Production of Phenylalanine

Pathway alterations for the production of phenylalanine are similar to the above except at the terminal pathways leading to phenylalanine. These include (1) the overexpression of the enzymes from chorismate to phenylalanine; (2) deletion of trip operon; and (3) deletion of phenylalanine degrading enzymes, and (4) desensitize all the enzymes from DAHP to phenylalanine so that they are not inhibited by the latter.

To produce phenylalanine, an *E. coli* mutant (W3110 Δtrp Δtyr Δphe) (ref: Forberg, Eliaeson, and Haggstrom, 1988) can be used as a host. Plasmids pAT1 and pPS341 (or pPS706, pPSL706) can then be transformed into this strain. In addition, the $pheA^{fbr}$ gene from plasmid pJN6 (same ref) can be cut and ligated into either pPS341 or pAT1. The resulting stain can be cultured in the following medium containing, per liter; $NH_4CL$, 5 g; $K_2SO_4$, 0.8 g; $KH_2PO_4$, 0.5 g; $Na_2HPO_4$, 1 g; Na-citrate, 2.5 g; $FeCL_3$ $6H_2O$, 0.01 g; $CaCl_2$ $2H_2O$, 0.20; $MgCl_2$ $6H_2O$, 0.8 g; tryosine, 0.05 g; tryptophan, 0.025 g; glucose 10–30 g.

EXAMPLE 5
Production of tyrosine

Pathway alterations for the production of tyrosine are similar to the above except at the terminal pathways leading to tyrosine. These include (1) the overexpression of the enzymes from chorismate to tyrosine; (2) deletion of trp operon and the phenylalanine branch; (3) deletion of tyrosine degrading enzymes; and (4) desensitize all the enzymes from DAHP to tyrosine so that they are not inhibited by the later.

EXAMPLE 6
Production of indigo

Production of indigo may be achieved by converting tryptophan or an intermediate from the trp pathway to indigo, either in vitro or in vivo. Since the Pps technology increases the production of DAHP, it will also increase the supply of any metabolite that serve as the precursor for indigo. To produce indigo, the tryptophan producing strain described above can be used as a host. However, the strain needs to be made tna+ and overexpressing naphthalene dioxygenase from *Pseudomonas putida*. In this strain, tryptophan produced will be degraded by tryptophanase to indole, which is then converted to cis-indole-2, 3-dihydrodiol by the cloned naphthalene dioxygenase. The cis-indole-2, 3-dihydrodiol produced is spontaneously converted to indigo in the presence of oxygen. ATCC 31743 is the strain used in conversion of DAHP to tryptophan.

EXAMPLE 7
Production of quinoid organics

Quinoid organics can be derived from dehydroquinate which is a down-stream metabolite of DAHP. To produce quinic acid, *E. coli* AB2848 aroD harboring pTW8090A which contains the gene qad (quinic acid dehydrogenase from *Klebsiella pneumoniae*) (ref: Draths, Ward, and Frost, 1992, JACS, 114, 9725–9726), and pKD136 (ref: same as above) which contains tkt, aroF, and aroB genes can be used as a host. The pps gene can be cloned into one of these plasmids and be simultaneously overexpressed. It has been reported that at least 80 mM of D-glucose can be converted into 25 mM of quinic acid. After cell removal, quinic acid in the supernatant can be converted into benzoquinone after addition of sulfuric acid and technical grade manganese (IV) dioxide and heating at 100° C. for 1 h. In the absence of acidification, aqueous solutions of purified quinic acid are converted to hydroquinone in 10% yield upon heating at 100° C. for 18 h with technical grade manganese dioxide.

EXAMPLE 8
Production of Catechol

Production of catechol may be achieved by transforming pps into *E. Coli* expressing pKD136. Since the Pps technology increases the production of DAHP, it will also increase the supply of any metabolite that serves as the precursor for catechol.

EXAMPLE 9
Characterization of luxI'-driven pps expression

To characterize the luxI'-driven pps expression, pPS706 were transformed into AB2847/pRW5 and AB2847/pAT1, and the Pps activity was measured when the strains were cultured in either glucose or xylose medium. The Pps activity increased with the autoinducer (N-(3-xox-hexanoyl)-hmoserine lactone) concentration and reached saturation when 1 $\mu$M autoinducer was used. Pps activity in the same strain growing in xylose medium was the same as that in glucose. The Pps activity was independent of IPTG concentration (data not shown). Therefore, the inventor achieved the independent modulation of three key enzymes in the production of aromatics: AroG (IPTG-inducible), TktA (on/off or presence/absence) and Pps (autoinducer-inducible).

While in accordance with the patent statutes, the best mode and preferred embodiments of the invention have been described, it is to be understood that the invention is not limited thereto, but rather is to be measured by the scope and spirit of the appended claims.

What is claimed is:

1. A method of producing 3-deoxy-D-arabino-heptulosonate 7-phosphate (DAHP) comprising the steps of:
   (a) placing a microorganism with genetic elements comprising pps and tkt genes wherein said genes are expressed by said microorganism in a media comprising glucose solution;
   (b) overexpressing the pps and tkt genes of said microorganisms in the glucose media; and
   (c) recovering DAHP from said media.

2. The method of claim 1 including an added step of growing microorganisms in a growth media to a density of at least 5 times $10^9$ cell/ml.

3. The method of claim 1 wherein the pps gene is operably linked to a tac promoter.

4. The method of claim 1 wherein said microorganism is *Escherichia coli* AB2847.

5. The method of claim 1 wherein said microorganism comprises a plasmid selected from the group consisting of pPS341, pPSL706, and pPS706.

6. The method of claim 1 wherein said microorganism is a strain of *E. coli*.

7. The method of claim 6 wherein the strain of *E. coli* is AB2847 aroB.

8. A method of producing tryptophan comprising the steps of:
   (a) placing a microorganism with genetic elements comprising pps, tkt, and serA genes wherein said genes are expressed by said microorganism in a media comprising glucose solution;
   (b) overexpressing the pps, tkt, and serA genes of said microorganisms in the glucose media; and
   (c) recovering tryptophan from said media.

9. The method of claim 8 including an added step of growing microorganisms in a growth media to a density of at least 5 times $10^9$ cell/ml.

10. The method of claim 8 wherein the pps gene is operably linked to a tac promoter.

11. The method of claim 8 wherein said microorganism is *Escherichia coli* AB2847.

12. The method of claim 8 wherein said microorganism comprises a plasmid selected from the group consisting of pPS341, pPSL706, and pPS706.

13. The method of claim 8 wherein said microorganism is a strain of *E. coli*.

14. The method of claim 13 wherein the strain of *E. coli* is AB2847 aroB.

15. A method of producing phenylalanine comprising the steps of:
   (a) placing a microorganism with genetic elements comprising pps, tkt, and pheA$^{fbr}$ genes wherein said genes are expressed by said microorganism in a media comprising glucose solution;
   (b) overexpressing the pps, tkt, and pheA$^{fbr}$ genes in said microorganisms in said glucose media; and
   (c) recovering phenylalanine from said glucose media.

16. The method of claim 15 including an added step of growing microorganisms in a growth media to a density of at least 5 times $10^9$ cell/ml.

17. The method of claim 15 wherein the pps gene is operably linked to a tac promoter.

18. The method of claim 15 wherein said microorganism is *Escherichia coli* AB2847.

19. The method of claim 15 wherein said microorganism comprises a plasmid selected from the group consisting of pPS341, pPSL706, and pPS706.

20. The method of claim 15 wherein said microorganism is a strain of *E. coli*.

21. The method of claim 20 wherein the strain of *E. coli* is AB2847 aroB.

22. A method of producing quinic acid comprising the steps of:
   (a) placing a microorganism with genetic elements comprising pps, tkt, and qad genes wherein said genes are expressed by said microorganism in a media comprising glucose solution;
   (b) overexpressing the pps, tkt, and qad genes in said microorganisms in the glucose media; and
   (c) recovering quinic acid from said media.

23. The method of claim 22 including an added step of growing microorganisms in a growth media to a density of at least 5 times $10^9$ cell/ml.

24. The method of claim 22 wherein the pps gene is operably linked to a tac promoter.

25. The method of claim 22 wherein said microorganism is *Escherichia coli* AB2847.

26. The method of claim 22 wherein said microorganism comprises a plasmid selected from the group consisting of pPS341, pPSL706, and pPS706.

27. The method of claim 22 wherein said microorganism is a strain of *E. coli*.

28. The method of claim 27 wherein the strain of *E. coli* is AB2847 aroB.

29. The method of claim 1 including the step of further processing DAHP to obtain derivative products.

* * * * *

UNITED STATES PATENT AND TRADEMARK OFFICE
CERTIFICATE OF CORRECTION

PATENT NO. : 5,985,617
APPLICATION NO. : 09/277183
DATED : November 16, 1999
INVENTOR(S) : James C. Liao Page 1 of 1

It is certified that error appears in the above-identified patent and that said Letters Patent is hereby corrected as shown below:

In the Drawings

Fig. 1B, delete "SPECIFIC GRAVITY" and insert --SPECIFIC ACTIVITY--.

Signed and Sealed this

Twenty-ninth Day of January, 2008

JON W. DUDAS
*Director of the United States Patent and Trademark Office*